United States Patent
Lee et al.

(10) Patent No.: US 7,164,036 B2
(45) Date of Patent: Jan. 16, 2007

(54) BENZOPHENONE COMPOUND AND INK COMPOSITION INCLUDING THE SAME

(75) Inventors: Kyung-hoon Lee, Gyeonggi-do (KR); Seung-min Ryu, Gyeonggi-do (KR); Yeon-kyoung Jung, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 285 days.

(21) Appl. No.: 10/851,124

(22) Filed: May 24, 2004

(65) Prior Publication Data

US 2004/0237836 A1    Dec. 2, 2004

(30) Foreign Application Priority Data

May 27, 2003    (KR) ................. 10-2003-0033837

(51) Int. Cl.
*C09D 11/00*  (2006.01)
*C07C 69/94*  (2006.01)
*C07C 69/732*  (2006.01)
*C07C 235/80*  (2006.01)

(52) U.S. Cl. .................. 560/36; 560/101; 106/31.43; 106/31.58

(58) Field of Classification Search ............... 560/36, 560/101; 106/31.43, 31.58
See application file for complete search history.

(56) References Cited

U.S. PATENT DOCUMENTS

| 4,256,493 A * | 3/1981 | Yokoyama et al. ...... 106/31.58 |
| 6,346,595 B1 | 2/2002 | O'Lenick, Jr. |
| 6,369,267 B1 * | 4/2002 | Toan et al. ................. 560/144 |
| 6,803,395 B1 * | 10/2004 | Smith et al. ................ 523/160 |
| 6,811,596 B1 * | 11/2004 | Bedford et al. .......... 106/31.29 |

FOREIGN PATENT DOCUMENTS

JP    04-198148    *   7/1992

OTHER PUBLICATIONS

Castellan et al., Journal of Photochemistry and Photobiology, A: Chemistry, 84(3), 311-316, 1994.*
U.S. Appl. No. 10/851,161, filed May 24, 2004, Kyung-hoon Lee et al., Samsung Electronics Co., Ltd.

* cited by examiner

*Primary Examiner*—Fiona T. Powers
(74) *Attorney, Agent, or Firm*—Staas & Halsey LLP

(57) ABSTRACT

A benzophenone compound, and an ink composition that includes the benzophenone compound can absorb UV light, and thus improve lightfastness of images produced with the ink composition containing the compound. Due to the function of the benzophenone compound as a lightfast dispersant, the dispersibility and the lightfastness of an ink composition are improved with the benzophenone compound, without requiring an additional lightfastness enhancer.

18 Claims, No Drawings

BENZOPHENONE COMPOUND AND INK COMPOSITION INCLUDING THE SAME

CROSS-REFERENCE TO RELATED APPLICATIONS

This application claims the priority of Korean Patent Application No.2003-33837, filed on May 27, 2003, in the Korean Intellectual Property Office, the disclosure of which is incorporated herein in its entirety by reference.

BACKGROUND OF THE INVENTION

1. Field of the Invention

The present invention relates to a benzophenone compound and an ink composition that contains the same, and more particularly, to a benzophenone compound that improves the dispersibility and lightfastness of a colorant, and an ink composition that contains the benzophenone compound.

2. Description of the Related Art

In general, ink compositions for ink-jet printing contain a colorant, a solvent, and an additive such as a dispersing agent. A dye or a pigment may be used as the colorant. However, using a dye as the colorant is limited due to its poor waterfastness and lightfastness compared to a pigment.

One of common dispersing agents for such ink compositions is a polymeric dispersing agent that has both hydrophilic and hydrophobic groups. The hydrophobic group of the polymeric dispersing agent is responsible for the dispersibility of the colorant, whereas the hydrophilic group imparts steric stability to the colorant by interacting with an aqueous solvent.

However, the polymeric dispersing agent has a large molecular weight so that the physical properties, for example, the viscosity, of the ink composition are greatly affected even when there is a minor change in the amount of the polymeric dispersing agent. Accordingly, it is difficult to control the amount of the dispersing agent when preparing an ink composition. In addition, although the polymeric dispersing agent has hydrophilic groups in its molecular structure, the hydrophilic fraction in the polymeric compound is insufficient to allow the composition to fully dissolve in water, and a significant amount of time is required.

In general, a medium, such as paper, after printing with such an ink composition is exposed to moist air and/or sunlight, so that ink compositions that are effectively lightfast and waterfast are required.

As a method for improving the lightfastness of an ink composition, adding a large molecular weight silicon compound to the ink composition as a lightfast additive for a UV blocking effect was suggested (U.S. Pat. No. 6,346,595). However, the silicon compound has a complex structure and is less miscible with other components in the ink composition when it has a larger molecular weight. Furthermore, agglomeration and precipitation occur in the ink composition when it is stored for an extended period of time, failing to guarantee long-term storage stability.

SUMMARY OF THE INVENTION

The present invention provides a lightfast dispersing agent with improved ultraviolet rays (UV) absorbency and dispersibility.

The present invention also provides an ink composition that includes the lightfast dispersing agent to improve the lightfastness and dispersibility of a colorant.

In one aspect of the present invention, a benzophenone compound of formula (1) below is utilized:

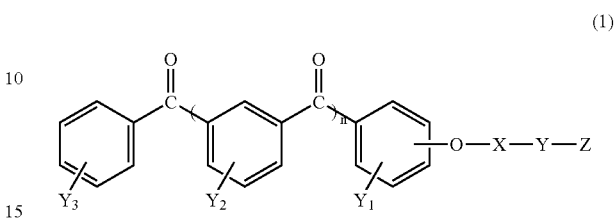

(1)

wherein $Y_1$ is one selected from the group consisting of a H, a OH, an $N(R_1)(R_2)$, a SH, and a substituted or unsubstituted $C_1$–$C_{30}$ heteroalkyl group; each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group; X is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group; Y is a linker selected from the group consisting of —O—, —CO—, —$NR_1$—, —N=N—, —S—, —NH—, —CH=CH—, —C≡C, —C(=O)$NR_1$—, —$NR_1$CO—, —$SO_2$—, —$SO_3$—, —COO—, —OCO—, —C(=S)—O—, —OC(=S)—, —CO—O—CO—, —CO—S—CO—, —CO—$NR_1$—CO—, —C(=S)—O—C(=S)—, —C(=S)—S—C(=S)—, —C(=S)—$NR_1$—C(=S)—, —NHCO—$R_3$—COO—, —OCO—$R_3$—CONH—, —OCO—$R_3$—COO—, —O—P(=O)(OH)—O—, and —O—P(OH)—O—; and Z is a moiety of one of formulas (2) and (3) below:

$$-\!\!\!-\!(CH_2CH_2O)_a\!-\!(CH_2CHO)_b\!-\!(CH_2CH_2O)_c\!-\!H \atop |\phantom{-------}CH_3} \quad (2)$$

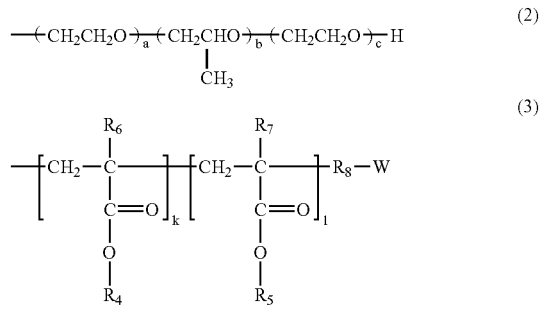

(3)

wherein each of $R_1$ and $R_2$ is independently one of a hydrogen atom and a $C_1$–$C_6$ alkyl group; n is an integer from 0 to 6; $R_3$ is selected from the same group for said X; each of a, b, and c is independently an integer from 1 to 20; each of $R_4$ and $R_5$ is independently a $C_1$–$C_{10}$ alkyl group; each of $R_6$ and $R_7$ is independently one of a hydrogen atom and a methyl group; $R_8$ is one of a substituted or unsubstituted $C_1$–$C_{20}$ alkylene group and a substituted or unsubstituted $C_6$–$C_{20}$ arylene group; W is one of —COOH, —NH$_2$, and —OH; and each of k and l is independently an integer from 1 to 10.

In another aspect of the present invention, an ink composition includes: a colorant; at least one of the benzophenone compounds of formula (1) above; and an aqueous medium.

Additional aspects and/or advantages of the invention will be set forth in part in the description which follows and, in part, will be obvious from the description, or may be learned by practice of the invention.

DETAILED DESCRIPTION OF THE PREFERRED EMBODIMENTS

Reference will now be made in detail to the embodiments of the present invention, examples of which are illustrated in the accompanying drawings, wherein like reference numerals refer to the like elements throughout. The embodiments are described below to explain the present invention by referring to the figures.

Embodiments of a benzophenone compound that is a lightfast dispersing agent and an ink composition that contains the benzophenone compound, according to embodiments of the present invention, will now be described in detail.

A benzophenone compound of formula (1) below according to embodiments of the present invention serves as a lightfast dispersing agent, and thus improves the dispersibility and lightfastness of an ink composition when added thereto without requiring an additional lightfast material.

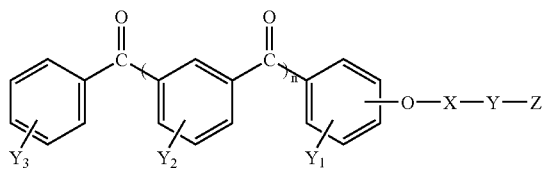

(1)

In formula (1), $Y_1$ is one selected from the group consisting of a H, a OH, an $N(R_1)(R_2)$, a SH, and a substituted or unsubstituted $C_1$–$C_{30}$ heteroalkyl group; each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group; X is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group; Y is a linker selected from the group consisting of —O—, —CO—, —NR$_1$—, —N=N—, —S—, —NH—, —CH=CH—, —C≡C—, —C(=O)NR$_1$—, —NR$_1$CO—, —SO$_2$—, —SO$_3$—, —COO—, —OCO—, —C(=S)O—, —OC(=S)—, —CO—O—CO—, —CO—S—CO—, —CO—NR$_1$—CO—, —C(=S)—O—C(=S)—, —C(=S)—S—C(=S)—, —C(=S)—NR$_1$—C(=S)—, —NHCO—R$_3$—COO—, —OCO—R$_3$—CONH—, —OCO—R$_3$—COO—, —O—P(=O)(OH)—O—, and —O—P(OH)—O—; and Z is a moiety of one of formulas (2) and (3) below:

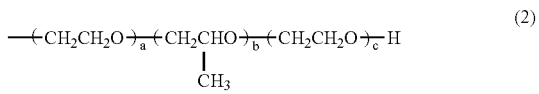

(2)

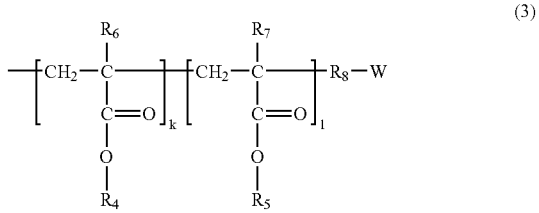

(3)

wherein each of $R_1$ and $R_2$ is independently one of a hydrogen atom and a $C_1$–$C_6$ alkyl group; n is an integer from 0 to 6; $R_3$ is selected from the same group for said X; each of a, b, and c is independently an integer from 1 to 20; each of $R_4$ and $R_5$ is independently a $C_1$–$C_{10}$ alkyl group; each of $R_6$ and $R_7$ is independently one of a hydrogen atom and a methyl group; $R_8$ is one of a substituted or unsubstituted $C_1$–$C_{20}$ alkylene group and a substituted or unsubstituted $C_6$–$C_{20}$ arylene group; W is one of —COOH, —NH$_2$, and —OH; and each of k and l is independently an integer from 1 to 10.

As is apparent from formula (1), the benzophenone compound according to embodiments of the present invention includes a benzophenone compound with a non-complex structure and a compound having moieties capable of enhancing the dispersibility and stability of a colorant, which are bound together via the linker Y. The linker Y may be an amide bond, an ester bond, a carbonyl bond, a sulfonyl bond, or the like. In other words, the benzophenone compound of formula (1) is synthesized by chemical reaction between a benzophenone compound of formula (4) below, which has a relatively simple structure, and a compound having such moieties.

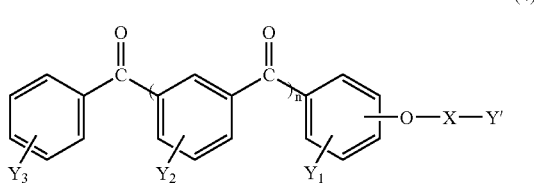

(4)

In formula (4), $Y_1$, $Y_2$, $Y_3$, n, and X are the same as in formula (1); and Y' is a reactive functional group that is selected from the group consisting of a carboxyl group, a hydroxyl group, an amino group, a sulfonic acid group, and a phosphoric acid group, and so forth.

As illustrated in reaction schemes (1) through (4) below, the benzophenone compound of formula (1) according to the present invention is formed by condensation between the reactive functional group Y', which may be a carboxyl group, a hydroxyl group, an amino group, a sulfonic acid group, and a phosphoric acid group, in the benzophenone compound of formula (4) and a reactive function group, which may be a carboxyl group, a hydroxyl group, an amino group, a sulfonic acid group, and a phosphoric acid group, or the like, in the compound having the moieties capable of enhancing the dispersibility and stability of the colorant.

Reaction scheme (1)

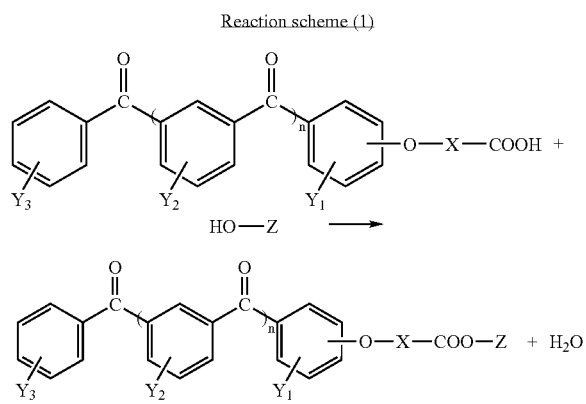

Reaction scheme (2)

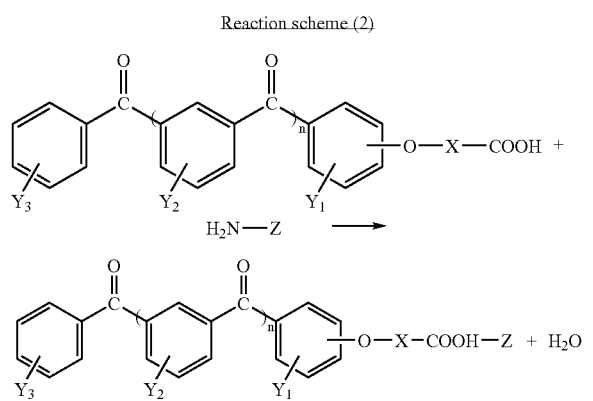

Reaction scheme (3)

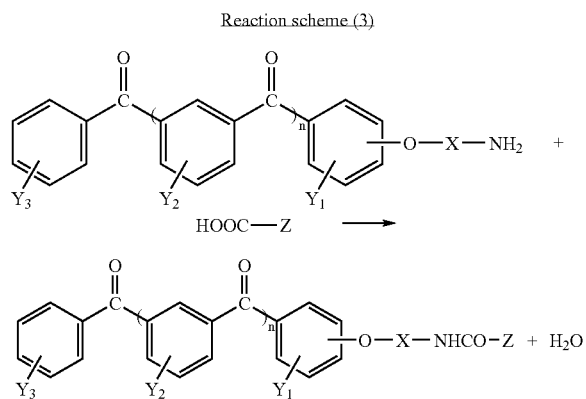

Reaction scheme (4)

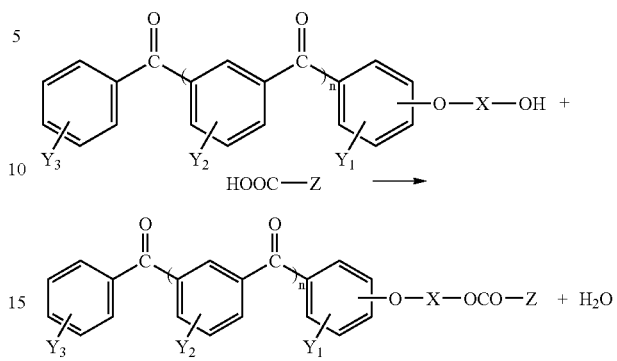

In reaction schemes (1) through (4) above, $Y_1$, $Y_2$, $Y_3$, Y, n, X, and Z are the same as indicated in formula (1). Compounds, which are chemically bound with the benzophenone compound of formula (4) and include moieties capable of enhancing the dispersibility and stability of a colorant as described above are expressed as HO—Y, $H_2N$—Y, and HOOC—Y in reaction schemes (1) through (4).

As described above, in formulas (1) through (4), $Y_1$ is one selected from the group consisting of a H, a OH, an $N(R_1)(R_2)$, a SH, and a substituted or unsubstituted $C_1$–$C_{30}$ heteroalkyl group, where each of $R_1$ and $R_2$ in the group of $N(R_1)(R_2)$ is independently a hydrogen atom or a straight or branched $C_1$–$C_6$ alkyl group.

$Y_1$ is a straight or branched heteroalkyl group having 1 to 30 carbon atoms, preferably, 1 to 20 carbon atoms, and more preferably, 1 to 10 carbon atoms. A $C_{10}$–$C_{30}$ heteroalkyl group for $Y_1$ implies a $C_1$–$C_{30}$ alkyl group including 1 to 3 hetero atoms selected from the group consisting of N, O, P, and S. Specific examples of such a heteroalkyl group include, but are not limited to, an oxymethyl group, an oxyethyl group, an oxypropyl group, a mercaptomethyl group, a mercaptoethyl group, a mercaptopropyl group, and the like. At least one hydrogen atom in the heteroalkyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

As described above, each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group. Each of $R_1$ and $R_2$ in the group of $N(R_1)(R_2)$ is independently a hydrogen atom or a straight or branched $C_1$–$C_6$ alkyl group. Nonlimiting, specific examples of $N(R_1)(R_2)$ include —$NH_2$, —NH($CH_3$), —N($CH_3$) —NH($CH_2CH_3$), —N($CH_2CH_3$)$_2$, and the like.

In particular, each of $Y_2$ and $Y_3$ may be a straight or branched alkyl group having 1 to 30 carbon atoms, preferably, 1 to 20 carbon atoms, and more preferably, 1 to 10 carbon atoms. Specific examples of such an alkyl group include, but are not limited to, a methyl group, an ethyl group, an n-propyl group, an isopropyl group, an n-butyl group, an isobutyl group, a sec-butyl group, a t-butyl group, a pentyl group, an iso-amyl group, a hexyl group, a heptyl group, an octyl group, a nonyl group, a decyl group, a dodecyl group, and the like, wherein at least one hydrogen atom in the alkyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, or the like.

Each of $Y_2$ and $Y_3$ may be a straight or branched heteroalkyl group having 1 to 30 carbon atoms, preferably, 1 to 20 carbon atoms, and more preferably, 1 to 10 carbon atoms. A $C_{10}$–$C_{30}$ heteroalkyl group for each of $Y_1$ and $Y_3$ implies a $C_1$–$C_{30}$ alkyl group including 1 to 3 hetero atoms selected from the group consisting of N, O, P, and S. Specific examples of such a heteroalkyl group include, but are not limited to, an oxymethyl group, an oxyethyl group, an oxypropyl group, a mercaptomethyl group, a mercaptoethyl group, a mercaptopropyl group, and the like. At least one hydrogen atom in the heteroalkyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

Each of $Y_2$ and $Y_3$ may be a straight or branched alkenyl group having 1 to 30 carbon atoms, preferably, 1 to 20 carbon atoms, and more preferably, 1 to 10 carbon atoms. The alkenyl group refers to an alkyl group which includes at least one carbon-carbon double bond in its molecular structure. Specific examples of such an alkenyl group include, but are not limited to, an ethylene group, a propylene group, a butylene group, a hexylene group, an allyl group, and the like. At least one hydrogen atom of the alkenyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

Each of $Y_2$ and $Y_3$ may be a straight or branched alkynyl group having 1 to 30 carbon atoms, preferably, 1 to 20 carbon atoms, and more preferably, 1 to 10 carbon atoms. The alkynyl group refers to an alkyl group which includes at least one carbon-carbon triple bond in its molecular structure. Specific examples of such an alkynyl group include, but are not limited to, an acetinyl group, a propynyl group, and the like. At least one hydrogen atom of the alkynyl group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

Each of $Y_2$ and $Y_3$ may be an aryl group having 6 to 30 carbon atoms, preferably, 6–18 carbon atoms, and more preferably, 6 to 12 carbon atoms, the aryl group being a hydrocarbon group that includes at least one aromatic ring. Specific examples of such an aryl group include, but are not limited to, aromatic radicals, such as phenyl, naphthyl, biphenyl, tetrahydronaphthyl, indanyl, and the like, with phenyl and naphthyl being preferred. At least one hydrogen atom in the aryl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

A substituted or unsubstituted arylalkyl group for each of $Y_2$ and $Y_3$ may have 7 to 30 carbon atoms, preferably, 7 to 19 carbon atoms, and more preferably, 7 to 13 carbon atoms. Specific examples of such an arylalkyl group include, but are not limited to, benzyl, phenetyl, triphenylmethyl, diphenylmethyl, phenylbutyl, neophyl, and the like. At least one hydrogen atom in the arylalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like. The arylalkyl group for each of $Y_2$ and $Y_3$ may include a carbon-carbon double bond or carbon-carbon triple bond in its alkyl residue, like a styryl group.

A substituted or unsubstituted heteroaryl group for each of $Y_2$ and $Y_3$ may have 3 to 30 carbon atoms, preferably, 3 to 18 carbon atoms, and more preferably, 3 to 12 carbon atoms. The heteroaryl group refers to an aryl group that contains one, two, or three hetero atoms, as atom(s) forming an aromatic ring skeleton, selected from the group consisting of N, O, P, and S, wherein at least one of the hetero atoms may be oxidized or quaternarized into, an N-oxide or a quaternary salt. Examples of such a heteroaryl group include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, an N-oxide and a quaternary salt of the foregoing materials, for example, pyridyl N-oxide, quinolinyl N-oxide, and the like. At least one hydrogen atom in the heteroaryl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

A substituted or unsubstituted heteroarylalkyl group for each of $Y_2$ and $Y_3$ may have 4 to 30 carbon atoms, preferably, 4 to 18 carbon atoms, and more preferably, 4 to 12 carbon atoms. The heteroarylalkyl group refers to an arylalkyl group containing one, two, or three heteroatoms, as atom(s) forming an aromatic ring skeleton, selected from the group consisting of N, O, P, and S. Examples of such a heteroarylalkyl group include, but are not limited to, thienylmethyl, thienylethyl, benzothienylmethyl, benzothienylethyl, pyridylmethyl, pyridylethyl, pyridylpropyl, pyrazinylmethyl, pyrazinylethyl, pyrimidinylmethyl, pyrimidinylethyl, pyridazinylmethyl, pyridazinylethyl, quinolinylmethyl, quinolinylethyl, quinoxalinylmethyl, quinoxalinylethyl, imidazolylmethyl, imidazolylethyl, furanylmethyl, furanylethyl, and the like. At least one hydrogen atom in the heteroarylalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

In formulas (1) and (4) above, X is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group. The alkylene group, the alkenylene group, the alkynylene group, the heteroalkylene group, the arylene group, the arylenealkylene (or alkylenearylene) group, the heteroarylene group, and the heteroarylenealkylene (or heteroalkylenearylene) group are divalent radicals incorporated in the middle of compounds, not monovalent radicals positioned at an end of compounds, and correspond to an alkyl group, an alkenyl group, an alkynyl group, a heteroalkyl group, an aryl group, an arylalkyl group, a heteroaryl group, and a heteroarylalkyl group, respectively.

An alkylene group for X may be a straight or branched radical having 1 to 30 carbon atoms, preferably, 1 to 20 carbon atoms, and more preferably, 1 to 10 carbon atoms. Specific examples of such an alkylene group include, but are not limited to, a methylene group, an ethylene group, an n-propylene group, an isopropylene group, an n-butylene group, an isobutylene group, a sec-butylene group, a t-butylene group, an n-pentylene group, a sec-pentylene group, a t-pentylene group, a hexylene group, a heptylene group, an octylene group, a nonylene group, a decylene group, a dodecylene group, and the like. At least one hydrogen atom in the alkylene group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

An alkenylene group or alkynylene group for X may have 1 to 30 carbon atoms, preferably, 1 to 20 carbon atoms, and more preferably, 1 to 10 carbon atoms. The alkenylene group and the alkynylene group differ from alkylene groups only in that they have at least one carbon-carbon double bond or carbon-carbon triple bond, respectively. At least one hydrogen atom in the alkenylene or alkynylene group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

A heteroalkylene group for X may have 1 to 30 carbon atoms, preferably, 1 to 20 carbon atoms, and more preferably, 1 to 10 carbon atoms. The heteroalkylene group refers to an alkylene group which includes one, two, or three hetero atoms selected from the group consisting of N, O, P, and S. Specific examples of such a heteroalkylene group include an oxymethylene group, an oxyethylene group, an oxypropoxy group, a mercaptomethylene group, a mercaptoethylene group, a mercaptopropoxy group, and the like. At least one hydrogen atom in the heteroalkylene group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

An arylene group for X may have 6 to 30 carbon atoms, preferably, 6 to 18 carbon atoms, and more preferably, 6 to 12 carbon atoms. Specific examples of such an arylene group include, but are not limited to, aromatic groups, such as a phenylene group, a naphthylene group, a biphenylene group, a tetrahydronaphthylene group, an indanylene group, and the like, with the phenylene group, biphenylene group, and nathphylene group being preferred. At least one hydrogen atom in the arylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

An arylenealkylene group for X may have 7 to 30 carbon atoms, preferably, 7 to 19 carbon atoms, and more preferably, 7 to 13 carbon atoms. The arylenealkylene group refers to a divalent radical corresponding to the arylalkyl group. Specific examples of such an arylenealkylene group include, but are not limited to, a methylenephenylene group, an ethylenephenylene group, a methylenenaphthylene group, an ethylenenaphthylene group, a methylenebiphenylene group, an ethylenebiphenylene group, an n-propylenephenylene group, an iso-propylenephenylene group, and the like. At least one hydrogen atom in the arylenealkylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

A heteroarylene group for X may have 3 to 30 carbon atoms, preferably, 3 to 18 carbon atoms, and more preferably, 3 to 12 carbon atoms. The heteroarylene group refers to an arylene group containing one, two, or three hetero atoms, as atom(s) forming an aromatic ring skeleton, selected from the group consisting of N, O, P, and S wherein at least one of the heteroatoms oxidized or quaternarized into, for example, an N-oxide or a quaternary salt. Specific examples of such a heteroarylene group include, but are not limited to, thienylene, benzothienylene, pyridylene, pyrazinylene, pyrimidinylene, pyridazinylene, quinolinylene, quinoxalinylene, imidazolylene, furanylene, benzofuranylene, thiazolylene, isoxazolylene, benzisoxazolylene, benzimidazolylene, triazolylene, pyrazolylene, pyrrolylene, indolylene, 2-pyridonylene, 4-pyridonylene, N-alkyl-2-pyridonylene, pyrazinonylene, pyridazinonylene, pyrimidinonylene, oxazolonylene, an N-oxide of the foregoing groups, such as pyridylene N-oxide and quinolinylene N-oxide, and a quaternary salt of the foregoing groups. At least one hydrogen atom in the heteroarylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

A heteroarylenealkylene group for X may have 4 to 30 carbon atoms, preferably, 4 to 18 carbon atoms, and more preferably, 4 to 12 carbon atoms. The heteroarylenealkylene group refers to a heteroarylene group which has alkylene groups substituted for some hydrogen atoms. Specific examples of such a heteroarylenealkylene group include, but are not limited to, thienylene methylene, thienylene ethylene, benzothienylene methylene, benzothienylene ethylene, pyridylene methylene, pyridylene ethylene, pyrazinylene methylene, pyrazinylene ethylene, pyrimidinylene methylene, pyrimidinylene ethylene, pyridazinylene methylene, pyridazinylene ethylene, quinolinylene methylene, quinolinylene ethylene, quinoxalinylene methylene, quinoxalinylene ethylene, imidazolylene methylene, imidazolylene ethylene, furanylene methylene, furanylene ethylene, and the like. At least one hydrogen atom in the heteroarylene-alkylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

As described above, the linker Y in formula (1) is a chemical bond selected from the group consisting of —O—, —CO—, —NR$_1$—, —N=N—, —S—, —NH—, —CH=CH—, —C≡C—, —C(=O)NR$_1$—, —NR$_1$CO—, —SO$_2$—, —SO$_3$—, —COO—, —OCO—, —C(=S)—O—, —OC(=S)—, —CO—O—CO—, —CO—S—CO—, —CO—NR$_1$—CO—, —C(=S)—O—C(=S)—, —C(=S)—S—C(=S)—, —C(=S)—NR$_1$—C(=S)—, —NHCO—R$_3$—COO—, —OCO—R$_3$—CONH—, —OCO—R$_3$—COO—, —O—P(=O)(OH)—O—, and —O—P(OH)—O—, wherein R$_1$ is a hydrogen atom or a straight or branched C1-C6 alkyl group, and R$_3$ is selected from the same group as for the X.

The Z in formula (1) above, which imparts the dispersibility and stability to the benzophenone compound of formula (1) above with regard to a colorant, may have one of the following formulas (2) and (3).

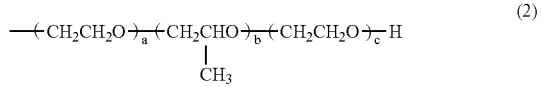

(2)

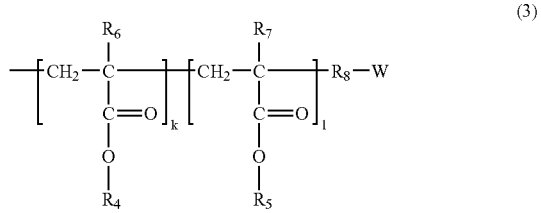

(3)

wherein each of R$_4$ and R$_5$ is independently an alkyl group having 1 to 10 carbon atoms, preferably, 1 to 7 carbon atoms, and more preferably, 1 to 4 carbon atoms; each of R$_6$ and R$_7$ is independently a hydrogen atom or a methyl group; and R$_8$ is a substituted or unsubstituted C$_1$–C$_{20}$ alkylene group or a substituted or unsubstituted C$_6$–C$_{20}$ arylene group.

The alkylene group for R8 in formula (3) may be a straight or branched radical that has 1 to 20 carbon atoms, preferably, 1 to 10 carbon atoms. Specific examples of such an alkylene group include, but are not limited to, a methylene group, an ethylene group, an n-propylene group, an isopropylene group, an n-butylene group, an isobutylene group, a sec-butylene group, a t-butylene group, an n-pentylene group, a sec-pentylene group, a t-pentylene group, a hexylene group, a heptylene group, an octylene group, a nonylene group, a decylene group, a dodecylene group, and the like. At least one hydrogen atom in the alkylene group may be substituted with a halogen atom, a haloalkyl group, an alkoxyl group, a hydroxyl group, a nitro group, a cyano group, an amino group, a lower alkylene amino group, an amidino group, hydrazine, hydrazone, a carboxyl group or a salt thereof, a sulfonic acid group or a salt thereof, a phosphoric acid group or a salt thereof, and the like.

The arylene group for R$_8$ in formula (3) may have 6 to 20 carbon atoms, preferably, 6 to 12 carbon atoms. Specific examples of such an arylene group include, but are not limited to, aromatic groups, such as a phenylene group, a naphthylene group, a biphenylene group, a tetrahydronaphthylene group, an indanylene group, and the like, with the phenylene group, biphenylene group, and nathphylene group being preferred. At least one hydrogen atom in the arylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

The W in formula (3) is —COOH, —NH$_2$, or —OH. In formulas (2) and (3), each of a, b, and c is an integer from 1 to 20, each of k and l is an integer from 1 to 10.

Specific examples of the benzophenone compound of formula (1) according to the present invention include benzophenone compounds of formulas (5) through (9) below.

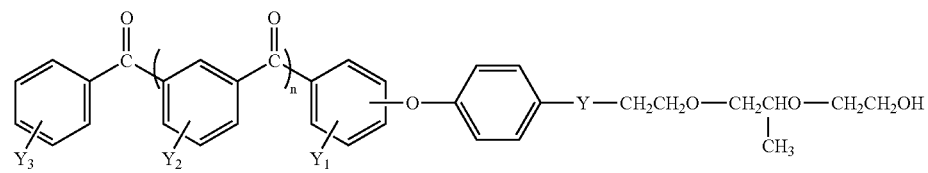

(5)

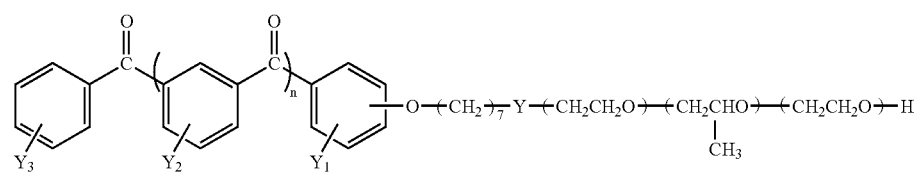

(6)

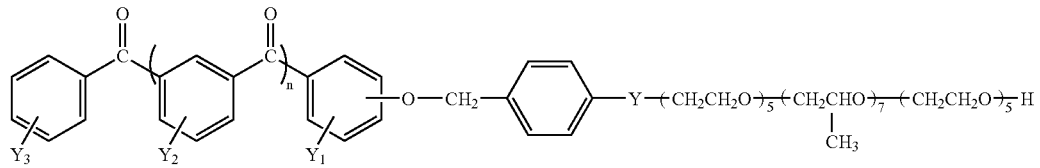

(7)

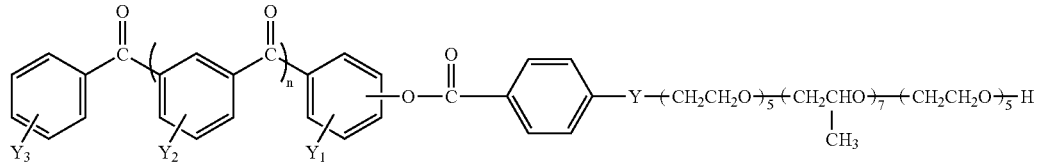

(8)

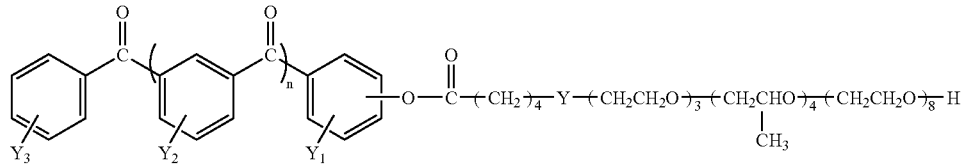

(9)

In formulas (5) through (9) above, $Y_1$, $Y_2$, $Y_3$, Y, and n are the same as in formula (1) above.

Hereinafter, an ink composition that includes the above benzophenone compound of formula (1) according to the present invention will be described in detail.

An ink composition according to an embodiment of the present invention includes a functional additive that is the benzophenone compound of formula (1) above to improve the dispersibility and lightfastness of a colorant. An ink composition according to an embodiment of the present invention may include a colorant, the bezophenone compound of formula (1), and an aqueous medium.

In the ink composition according to the present invention, the amount of the colorant may be in the range of 0.1–20 parts by weight, preferably, 0.5–15 parts by weight, with respect to 100 parts by weight of the ink composition.

Both inorganic and organic pigments may be used as the colorant in the ink composition according to the present invention. Specific examples of a pigment that may be used in the present invention include, but are not limited to, carbon black, graphite, vitreous carbon, activated charcoal, activated carbon, anthraquinones, phthalocyanine blue, phthalocyanine green, diazos, monoazos, pyranthrones, perylenes, quinacridones, and indigoid pigments.

The particle size of pigments significantly affects wettability, color strength, and glossiness. A pigment used as the colorant in the present invention may have a particle diameter that is small enough to pass 10–50 μm nozzles.

In the ink composition according to the present invention, the amount of the benzophenone compound of formula (1) may be in the range of 0.1–40 parts by weight, preferably, 0.5–20 parts by weight, and more preferably, 1–10 parts by weight, with respect to 100 parts by weight of the ink composition. If the amount of the benzophenone compound is less than 0.1 parts by weight, improvements in colorant's dispersibility and lightfastness are trivial. If the amount of the benzophenone compound is greater than 40 parts by weight, the ink composition is too thick to effectively disperse the colorant.

In the ink composition according to the present invention, the colorant and the benzophenone compound of formula (1) are dissolved or dispersed in an aqueous medium.

The aqueous medium may be water alone or a mixture of 5–50% by weight of an organic solvent and 50–95% by weight of water. A mixture of 5–35% by weight of an organic solvent and 65–95% by weight of water is preferred. When a mixture of water and an organic solvent is used as the aqueous medium, the ratio of water and the organic solvent may be varied depending on various factors, for example, desired characteristics, such as the viscosity, surface tension, drying speed, and the like, of the ink composition. Such characteristics of ink compositions vary depending on the printing methods of printers and the types of printing media.

Examples of a suitable organic solvent include, but are not limited to, alcohols, such as methyl alcohol, ethyl alcohol, n-propyl alcohol, isopropyl alcohol, n-butyl alcohol, sec-butyl alcohol, t-butyl alcohol, isobutyl alcohol, and the like; ketones, such as acetone, methylethyl ketone, diethyl ketone, diacetone alcohol, and the like; esters, such as methyl acetate, ethyl acetate, ethyl lactate, and the like; polyhydric alcohols, such as ethylene glycol, diethylene glycol, triethylene glycol, propylene glycol, butylene glycol, 1,4-butane diol, 1,2,4-butane triol, 1,5-pentane diol, 1,2,6-hexane triol, hexylene glycol, glycerol, glycerol ethoxylate, trimethylolpropane ethoxylate, and the like; ethers, such as ethylene glycol monomethyl ether, ethylene glycol monoethyl ether, diethylene glycol methyl ether, diethylene glycol ethyl ether, triethylene glycol monomethyl ether, triethylene glycol monoethyl ether, and the like; nitrogen-containing compounds, such as 2-pyrrolidone, N-methyl-2-pyrrolidone, and the like; and sulfur-containing compounds, such as dimethyl sulfoxide, tetramethylene sulfone, thioglycol, and the like.

Alternatively, the ink composition according to the present invention may further include an additive, for example, a viscosity adjuster, a surfactant, a wetting agent, and the like.

The viscosity adjuster of the ink composition adjusts the viscosity of the ink composition for smoother jetting. Specific examples of such a viscosity adjuster include, but are not limited to, casein, hydroxymethylcellulose, hydroxyethylcellulose, carboxymethylcellulose, and the like. The amount of the viscosity adjuster may be in the range of 0.1–5 parts by weight with respect to 100 parts by weight of the ink composition.

The amount of the surfactant may be in the range of 0.1–5.0 parts by weight with respect to 100 parts by weight of the ink composition. The surfactant of the ink composition affects the surface tension of the composition such that the ink composition is more stably jetted through a nozzle. An anionic surfactant or a nonionic surfactant may be used.

Examples of an anionic surfactant that may be used in the present invention include, but are not limited to, a salt of alkyl carboxylic acid having 2 to 1,000 carbon atoms, preferably, 10 to 200 carbon atoms, a salt of sulfonic acid having 2 to 1,000 carbon atoms, preferably, 10 to 200 carbon atoms, a salt of alkyl sulfonic acid ester having 2 to 1,000 carbon atoms, preferably, 10 to 200 carbon atoms, a salt of alkyl sulfonic acid having 2 to 1,000 carbon atoms, preferably, 10 to 200 carbon atoms, a salt of alkyl aryl sulfonic acid having 7 to 1,000 carbon atoms, preferably, 10 to 200 carbon atoms, and a mixture of the foregoing salts.

Examples of a nonionic surfactant that may be used in the present invention include, but are not limited to, polyoxyethylene alkyl ether having a $C_1$–$C_{1000}$, preferably, $C_{10}$–$C_{200}$, alkyl group, polyoxyethylene alkyl phenyl ether having a $C_1$–$C_{1000}$, preferably, $C_{10}$–$C_{200}$, alkyl group, polyoxyethylene secondary alkyl ether, a polyoxyethylene-oxypropylene block copolymer, polyglycerin fatty acid ester, sorbitan fatty acid ester, and a mixture of the foregoing materials.

The wetting agent prevents clogging of nozzles. The amount of the wetting agent may be in the range of 5–40 parts by weight with respect to 100 parts by weight of the ink composition. A polyhydric alcohol may be used as the wetting agent. Specific examples of a wetting agent that may be used in the present invention include, but are not limited to, glycerin, ethylene glycol, diethylene glycol, triethylene glycol, propylene glycol, dipropylene glycol, hexylene glycol, 1,3-butane diol, 1,4-butane diol, 1,5-pentane diol, 2-butene-1,4-diol, and a mixture of the foregoing alcohols.

Alternatively, the ink composition according to embodiments of the present invention may further include an acid or a base to improve the solubility of the benzophenone compound in the solvent and stabilize the pigment dispersed in the ink composition. The amount of the acid or base may be in the range of 0.1–5 parts by weight with respect to 100 parts by weight of the ink composition.

In an ink composition according to the present invention, the total amount of at least one additive selected from the group consisting of a viscosity adjuster, a surfactant, and a wetting agent may be in the range of 0.5–40 parts by weight with respect to 100 parts by weight of the ink composition.

A method of preparing the above ink composition, according to an embodiment of the present invention, will now be described.

A common colorant, the benzophenone compound of formula (1), and other additives, such as a dispersant, a viscosity adjuster, a surfactant, and the like, if required, are mixed together in an aqueous medium and thoroughly stirred to obtain a homogeneous composition. This composition is passed through a filter to provide an ink composition according to an embodiment of the present invention.

The benzophenone compound of formula (1) above according to the present invention may have various, non-limiting applications, for example, in liquid toner compositions, dry toner compositions, various paints, coating solutions, and the like.

The present invention will be described in greater detail with reference to the following examples. The following examples are for illustrative purposes and are not intended to limit the scope of the invention.

SYNTHESIS EXAMPLE 1

2-hydroxy-4-(4-carboxy)phenyloxybenzophenone was synthesized according to reaction scheme (5) below.

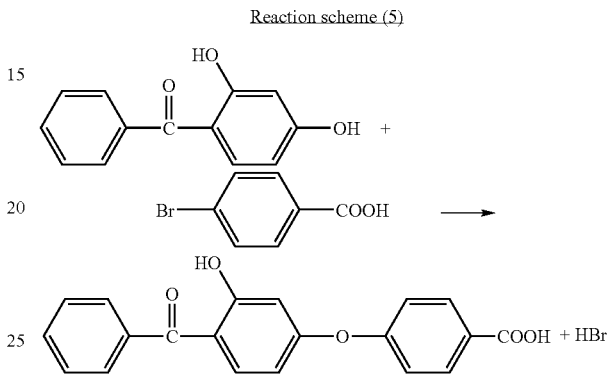

A 250-mL round-bottomed flask equipped with a reflux condenser was charged with 150 mL of dimethylformamide (DMF) and 10.7 g of 2,4-dihydxoxybenzophenone, and 1.2 g of sodium hydroxide was added into the flask in a nitrogen atmosphere and stirred. 10 g of 4-bromobenzoic acid was slowly added into the mixture, heated slowly to about 60° C. while stirring, and reacted for 5 hours. The reaction mixture was cooled to room temperature, and excess distilled water was added to the reaction product to precipitate it. Precipitates were filtered, washed several times with distilled water, and recrystallized using a solvent mixture of chloroform and ethanol to provide 9.5 g of 2-hydroxy-4-(4-carboxy)phenyloxybenzophenone.

SYNTHESIS EXAMPLE 2

2-hydroxy-4-(8-carboxy)octyloxybenzophenone was synthesized according to reaction scheme (6) below.

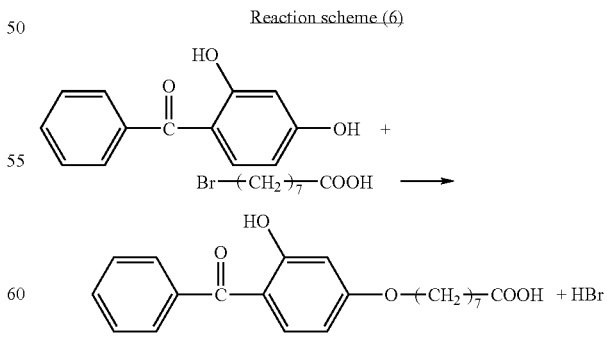

10 g of 2-hydroxy-4-(8-carboxy)octyloxybenzophenone was synthesized in the same manner as in Synthesis Example 1, except that 11.5 g of 8-bromooctanoic acid was used instead of 10 g of 4-bromobenzoic acid.

SYNTHESIS EXAMPLE 3

2-hydroxy-4-(4-carboxy)benzyloxybenzophenone was synthesized according to reaction scheme (7) below.

Reaction scheme (7)

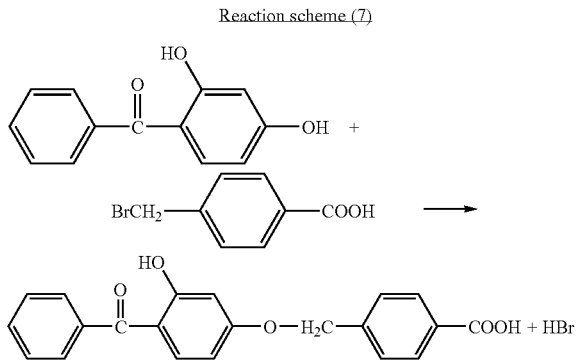

9.7 g of 2-hydroxy-4-(4-carboxy)bezyloxybenzophenone was synthesized in the same manner as in Synthesis Example 1, except that 10.5 g of α-bromo-p-toluic acid was used instead of 10 g of 4-bromobenzoic acid.

SYNTHESIS EXAMPLE 4

2-hydroxy-4-(4-carboxy)benzoyloxybenzophenone was synthesized according to reaction scheme (8) below.

Reaction scheme (8)

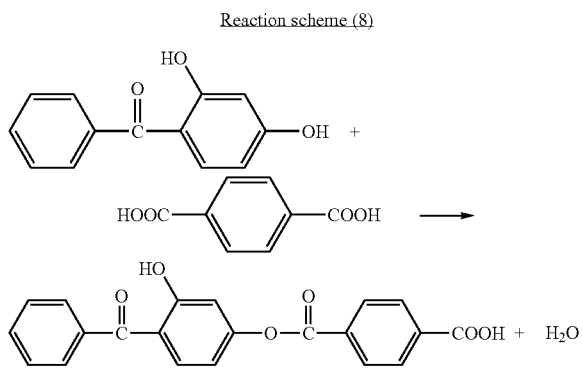

A 250-mL round-bottomed flask equipped with a reflux condenser was charged with 150 mL of dimethylsulfoxide (DMSO) and 8.5 g of terephthalic acid, and 6 g of thionyl chloride was added into the flask in a nitrogen atmosphere and stirred. 10.7 g of 2,4-dihydroxybenzophenone was slowly added into the mixture, heated slowly to about 60° C. while stirring, and reacted for 8 hours. The reaction mixture was cooled to room temperature, and excess distilled water was added to the reaction product to precipitate it. Precipitates were filtered, washed several times with distilled water, and recrystallized using a solvent mixture of chloroform and ethanol to provide 11.0 g of 2-hydroxy-4-(4-carboxy)benzoyloxybenzophenone.

SYNTHESIS EXAMPLE 5

2-hydroxy-4-(4-carboxy)butylcarbonyloxybenzophenone was synthesized according to reaction scheme (9) below.

Reaction scheme (9)

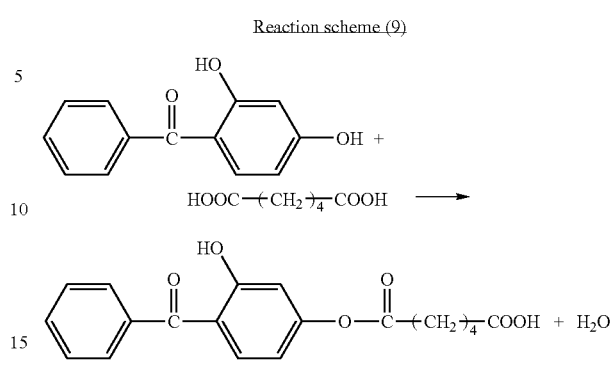

9.1 g of 2-hydroxy-4-(4-carboxy)butylcarbonyloxybenzophenone was synthesized in the same manner as in Synthesis Example 4, except that 7.3 g of adipic acid was used instead of 8.5 g of terephthalic acid.

SYNTHESIS EXAMPLE 6

2-hydroxy-4-(2-carboxy-1-methyl)ethylcarbonyloxybenzophenone was synthesized according to reaction scheme (10) below.

Reaction scheme (10)

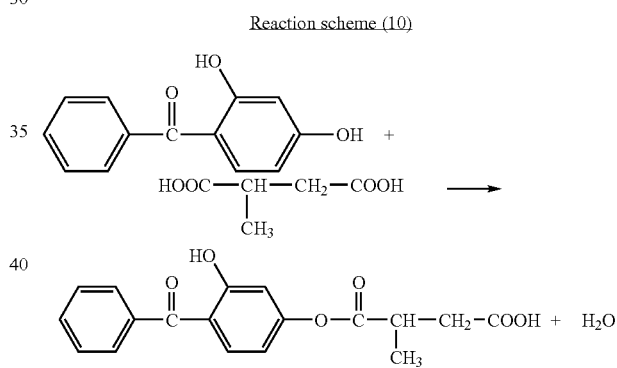

10.2 g of 2-hydroxy-4-(2-carboxy-1-methyl)ethylcarbonyloxybenzophenone was synthesized in the same manner as in Synthesis Example 4, except that 6.6 g of methyl succinic acid was used instead of 8.5 g of terephthalic acid.

SYNTHESIS EXAMPLE 7

2-hydroxy-4-(10-carboxy)decylcarbonyloxybenzophenone was synthesized according to reaction scheme (11) below.

Reaction scheme (11)

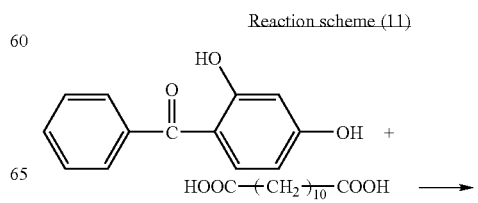

-continued

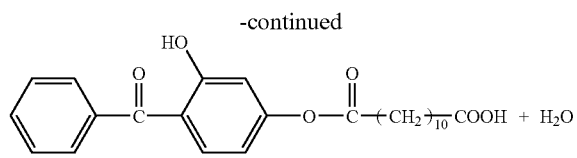

10.5 g of 2-hydroxy-4-(10-carboxy)decylcarbonyloxy-benzophenone was synthesized in the same manner as in Synthesis Example 4, except that 11.5 g of dodecanedioic acid was used instead of 8.5 g of terephthalic acid.

SYNTHESIS EXAMPLE 8

2-hydroxy-4-(4-amino)benzoyloxybenzophenone was synthesized according to reaction scheme (12) below.

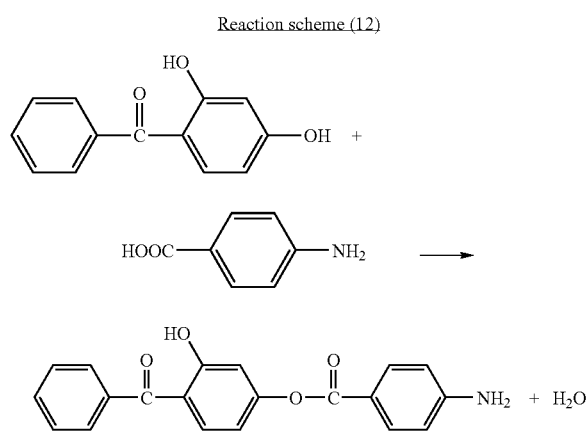

Reaction scheme (12)

10.9 g of 2-hydroxy-4-(4-amino)benzoyloxybenzophenone was synthesized in the same manner as in Synthesis Example 4, except that 6.9 g of 4-aminobenzoic acid was used instead of 8.5 g of terephthalic acid.

SYNTHESIS EXAMPLE 9

2-hydroxy-4-(5-amino)pentylcarbonyloxybenzophenone was synthesized according to reaction scheme (13) below.

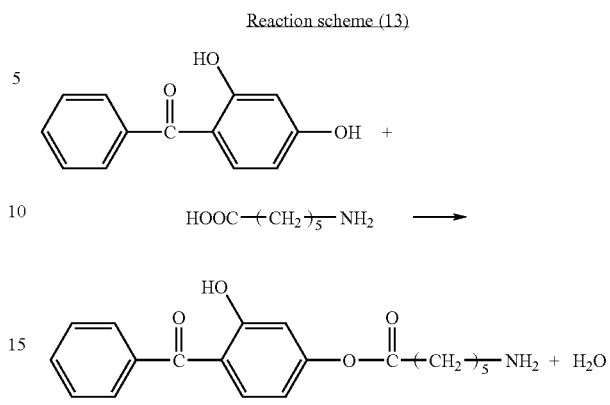

Reaction scheme (13)

10.4 g of 2-hydroxy-4-(5-amino)pentylcarbonyloxybenzophenone was synthesized in the same manner as in Synthesis Example 4, except that 6.6 g of 6-aminocaproic acid was used instead of 8.5 g of terephthalic acid.

SYNTHESIS EXAMPLE 10

A benzophenone compound of formula (11) below was synthesized from the benzophenone compound derived in Synthesis Example 1.

A 250-mL round-bottomed flask equipped with a reflux condenser was charged with 100 mL of ethyl acetate and 10.1 g the 2-hydroxy-4-(4-carboxy)phenyloxy-benzophenone derived in Synthesis Example 1 and stirred to dissolve the benzophenone compound. 5.5 g of alkoxylated alcohol of formula (10) below was put into the round-bottomed flask. 20 mL of conc. sulfuric acid was slowly added together with one or two boiling chips into the mixture and refluxed for 12 hours or longer. The reaction product was cooled to room temperature, and excess methanol was added to precipitate a desired crystalline compound. To remove unreacted products, the crystalline compound was dissolved in DMSO and precipitated with methanol. The crystalline precipitates were filtered and dried in a 60° C. oven to provide 10.1 g of the benzophenone compound of formula (11).

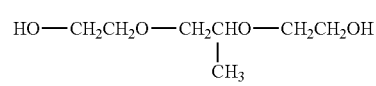

(10)

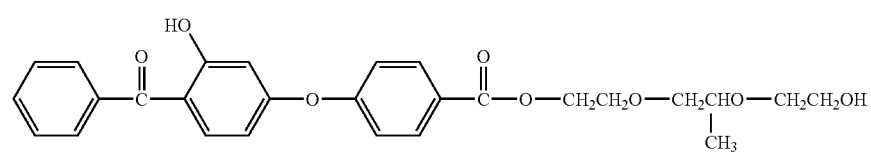

(11)

SYNTHESIS EXAMPLE 11

A benzophenone compound of formula (12) below was synthesized from the benzophenone compound derived in Synthesis Example 2.

9.8 g of the benzophenone compound of formula (12) was synthesized in the same manner as in Synthesis Example 10, except that 10.7 g of the 2-hydroxy-4-(8-carboxy)octyloxy-benzophenone obtained in Synthesis Example 2 and 5.5 g of the alkoxylated alcohol of formula (10) were used.

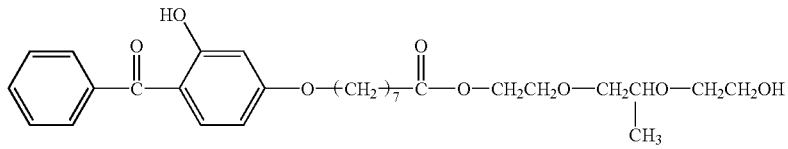
(12)

SYNTHESIS EXAMPLE 12

A benzophenone compound of formula (14) below was synthesized from the benzophenone compound derived in Synthesis Example 3.

19.7 g of the benzophenone compound of formula (14) was synthesized in the same manner as in Synthesis Example 10, except that 10.5 g of the 2-hydroxy-4(-4-carboxy)benzyloxybenzophenone obtained in Synthesis Example 3 and 26.3 g of alkoxylated alcohol of formula (13) below were used.

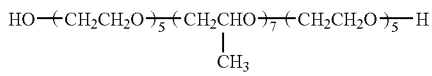
(13)

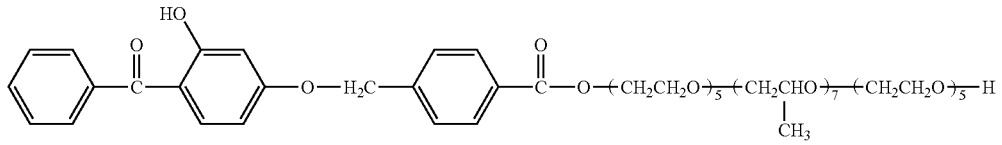
(14)

SYNTHESIS EXAMPLE 13

A benzophenone compound of formula (15) below was synthesized from the benzophenone compound derived in Synthesis Example 4.

20.4 g of the benzophenone compound of formula (15) was synthesized in the same manner as in Synthesis Example 10, except that 11.0 g of the 2-hydroxy-4-(4-carboxy)benzoyloxybenzophenone obtained in Synthesis Example 4 and 26.3 g of the alkoxylated alcohol of formula (13) were used.

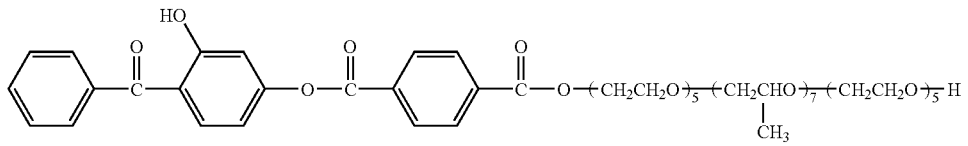
(15)

SYNTHESIS EXAMPLE 14

A benzophenone compound of formula (17) below was synthesized from the benzophenone compound derived in Synthesis Example 5.

18.8 g of the benzophenone compound of formula (17) was synthesized in the same manner as in Synthesis Example 10, except that 10.3 g of the 2-hydroxy-4(-4-carboxy)butylcarbonyloxybenzophenone obtained in Synthesis Example 5 and 22.1 g of alkoxylated alcohol of formula (16) below were used.

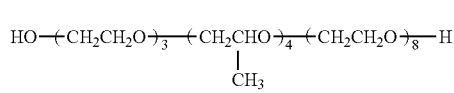
(16)

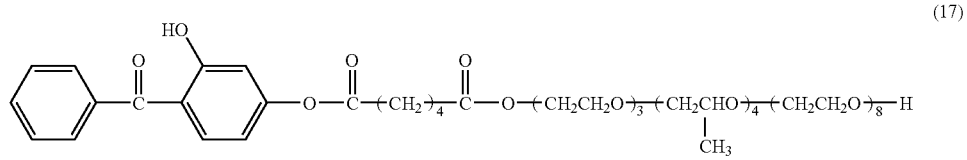
(17)

SYNTHESIS EXAMPLE 15

A benzophenone compound of formula (18) below was synthesized from the benzophenone compound derived in Synthesis Example 6.

17.3 g of the benzophenone compound of formula (18) was synthesized in the same manner as in Synthesis Example 10, except that 9.8 g of the 2-hydroxy-4-(2-carboxyl-1-methyl)ethylcarbonyloxybenzophenone obtained in Synthesis Example 6 and 22.1 g of the alkoxylated alcohol of formula (16) were used.

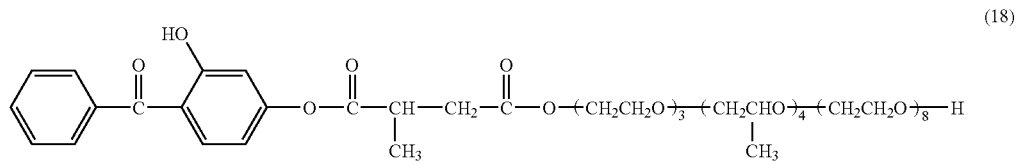
(18)

SYNTHESIS EXAMPLE 16

A benzophenone compound of formula (19) below was synthesized from the benzophenone compound derived in Synthesis Example 7.

12.1 g of the benzophenone compound of formula (19) was synthesized in the same manner as in Synthesis Example 10, except that 12.8 g of the 2-hydroxy-4-(10-carboxy)decylcarbonyloxybenzophenone obtained in Synthesis Example 7 and 5.5 g of the alkoxylated alcohol of formula (10) were used.

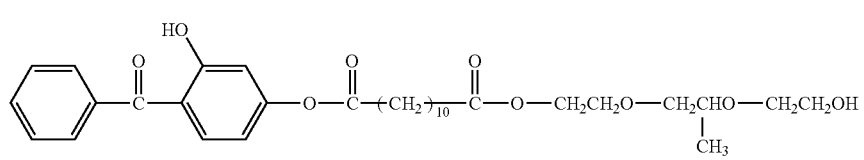
(19)

SYNTHESIS EXAMPLE 17

A benzophenone compound of formula (21) below was synthesized from the benzophenone compound derived in Synthesis Example 8.

19.1 g of the benzophenone compound of formula (21) was synthesized in the same manner as in Synthesis Example 10, except that 5.1 g of the 2-hydroxy-4-(4-amino) benzoyloxybenzophenone obtained in Synthesis Example 8 and 22.5 g of an acrylic copolymer (Mw=1500) of formula (20) below were used.

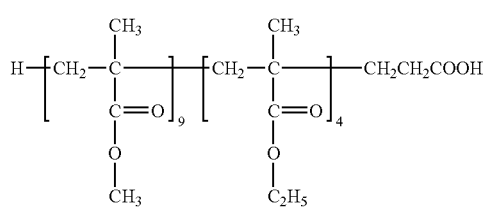

(20)

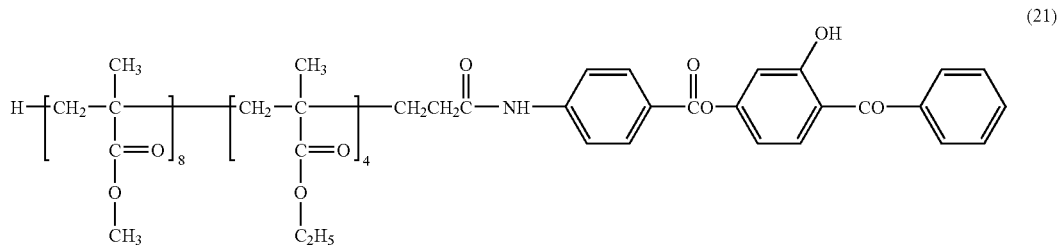

(21)

SYNTHESIS EXAMPLE 18

A benzophenone compound of formula (22) below was synthesized from the benzophenone compound derived in Synthesis Example 9.

17.3 g of the benzophenone compound of formula (22) was synthesized in the same manner as in Synthesis Example 10, except that 5.0 g of the 2-hydroxy-4-(5-amino) pentylcarbonyloxybenzophenone obtained in Synthesis Example 9 and 22.5 g of the acrylic copolymer of formula (20) were used.

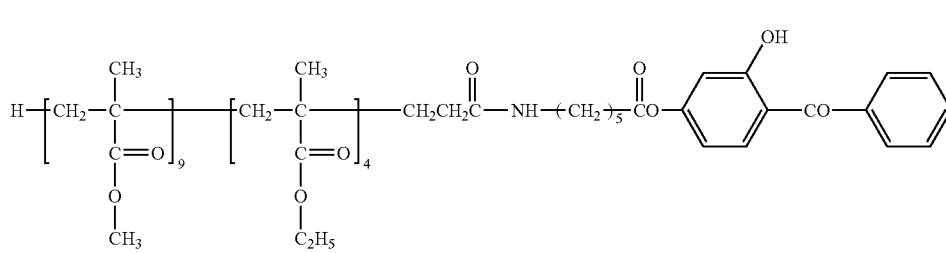

(22)

EXAMPLE 1

INK COMPOSITION

| COMPONENT | CONTENT |
| --- | --- |
| Colorant (carbon black) | 4.0 g |
| Water | 73.0 g |
| Isopropyl alcohol | 3.0 g |
| Glycerin | 8.0 g |
| Ethylene glycol | 8.0 g |
| Benzophenone compound of formula (11) | 4.0 g |

The above-listed components were mixed together and stirred for about 30 minutes or longer to obtain a homogeneous composition. This composition was passed through a 0.45-μm pore filter to provide an ink composition according to the present invention.

EXAMPLE 2

An ink composition according to the present invention was prepared in the same manner as in Example 1, except that the benzophenone compound of formula (12) was used instead of the benzophenone compound of formula (11).

EXAMPLE 3

An ink composition according to the present invention was prepared in the same manner as in Example 1, except that the benzophenone compound of formula (14) was used instead of the benzophenone compound of formula (11).

EXAMPLE 4

An ink composition according to the present invention was prepared in the same manner as in Example 1, except that the benzophenone compound of formula (15) was used instead of the benzophenone compound of formula (11).

EXAMPLE 5

An ink composition according to the present invention was prepared in the same manner as in Example 1, except that the benzophenone compound of formula (17) was used instead of the benzophenone compound of formula (11).

EXAMPLE 6

An ink composition according to the present invention was prepared in the same manner as in Example 1, except that the benzophenone compound of formula (18) was used instead of the benzophenone compound of formula (11).

EXAMPLE 7

An ink composition according to the present invention was prepared in the same manner as in Example 1, except that the benzophenone compound of formula (19) was used instead of the benzophenone compound of formula (11).

EXAMPLE 8

An ink composition according to the present invention was prepared in the same manner as in Example 1, except that the benzophenone compound of formula (21) was used instead of the benzophenone compound of formula (11).

EXAMPLE 9

An ink composition according to the present invention was prepared in the same manner as in Example 1, except that the benzophenone compound of formula (22) was used instead of the benzophenone compound of formula (11).

COMPARATIVE EXAMPLE 1

An ink composition was prepared in the same manner as in Example 1, except that TEGO dispers 750W (available from TEGO CO.) was used instead of the benzophenone compound of formula (11).

COMPARATIVE EXAMPLE 2

An ink composition was prepared in the same manner as in Example 1, except that TEGO wet 260 (available from TEGO CO.) was used instead of the benzophenone compound of formula (11).

COMPARATIVE EXAMPLE 3

An ink composition was prepared in the same manner as in Example 1, except that a styrene/acrylic acid copolymer was used instead of the benzophenone compound of formula (11).

COMPARATIVE EXAMPLE 4

An ink composition was prepared in the same manner as in Example 1, except that an arylamine/styrene sulfuric acid copolymer was used instead of the benzophenone compound of formula (11).

COMPARATIVE EXAMPLE 5

An ink composition was prepared in the same manner as in Example 1, except that an 4-vinylpyridine/maleic acid copolymer was used instead of the benzophenone compound of formula (11).

The properties of the ink compositions prepared in Examples 1 through 9 and Comparative Examples 1 through 5 were evaluated as follows.

Long-term Storage Stability Test 100 mL of samples of the ink compositions prepared in Examples 1 through 9 and Comparative Examples 1 through 5 were portioned into respective heat-resistant glass bottles. The glass bottles were sealed and stored in a 60° C. water bath for 2 months. It was observed whether precipitates appeared in the bottles. The results are shown in Table 1. In Table 1, 0 indicates that no precipitate appeared, and X indicates that precipitates appeared.

TABLE 1

| No. | Example | | | | | | | | | Comparative Example | | | | |
|---|---|---|---|---|---|---|---|---|---|---|---|---|---|---|
|  | 1 | 2 | 3 | 4 | 5 | 6 | 7 | 8 | 9 | 1 | 2 | 3 | 4 | 5 |
| Result | 0 | 0 | 0 | 0 | 0 | 0 | 0 | 0 | 0 | 0 | 0 | 0 | 0 | 0 |

As shown in Table 1, for the ink compositions prepared in Examples 1 through 9, which contain the benzophenone compound of formula (1), no precipitate appears, indicating that the ink compositions according to the present invention is as stable during long-term storage as the ink compositions of Comparative Examples 1 through 5, which contain the common dispersant TEGO dispers 750W.

Lightfastness Test

2×2 cm solid patterns were printed using the ink compositions of Examples 1 through 9 and Comparative Examples 1 through 5 and an ink jet printer (MJC 1130i, available from SAMSUNG ELECTRONICS CO.). The printed results were exposed to light for 100 hours in a Q-SUN Xenon Test Chamber. Optical density (OD) was measured before and after light exposure, and A values (lightfastness values) were calculated using the following equation. Lightfastness was evaluated as effective (0) for A≧90, moderate (Δ) for 75≦A<90, and poor (X) for A<75. The results are shown in Table 2.

$A = \text{OD after exposure/OD before exposure} \times 100 (\%)$

TABLE 2

| No. | Example | | | | | | | | | Comparative Example | | | | |
|---|---|---|---|---|---|---|---|---|---|---|---|---|---|---|
| | 1 | 2 | 3 | 4 | 5 | 6 | 7 | 8 | 9 | 1 | 2 | 3 | 4 | 5 |
| Result | 0 | 0 | 0 | 0 | 0 | 0 | 0 | 0 | 0 | X | X | X | X | X |

As shown in Table 2, the ink compositions prepared in Examples 1 through 9, which contain the benzophenone compound of formula (1), have effective lightfastness at A values of 90% or more. However, the ink compositions prepared in Comparative Examples 1 through 5 have lightfastness values of less then 75%. Evidently, the ink compositions according to the present invention, which contain the benzophenone compound of formula (1), have improved lightfastness compared to the conventional ink compositions.

As described above, the benzophenone compound of formula (1) above according to the present invention can absorb UV light and thus improve lightfastness of images produced with the ink composition containing it. Furthermore, the benzophenone compound of formula (1) improves the dispersibility of a colorant in an ink composition. Due to the function of the benzophenone compound of formula (1) as a lightfast dispersant, the dispersibility and the lightfastness of an ink composition can be improved with the benzophenone compound, without requiring an additional lightfastness enhancer.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A benzophenone compound of formula (1) below:

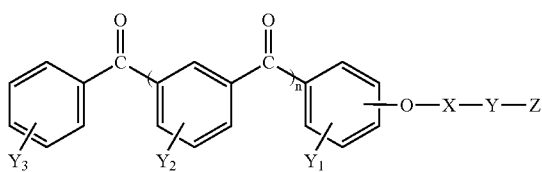

(1)

wherein $Y_1$ is one selected from the group consisting of a H, a OH, an $N(R_1)(R_2)$, a SH, and a substituted or unsubstituted $C_1$–$C_{30}$ heteroalkyl group;

each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

X is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

Y is a linker selected from the group consisting of —O—, —CO—, —NR$_1$—, —N=N—, —S—, —NH—, —CH=CH—, —C≡C—, —C(=O)NR$_1$—, —NR$_1$CO—, —SO$_2$—, —SO$_3$—, —COO—, —OCO—, —C(=S)—O—, —OC(=S)—, —CO—O—CO—, —CO—S—CO—, —CO—NR$_1$—CO—, —C(=S)—O—C(=S)—, —C(=S)—S—C(=S)—, —C(=S)—NR$_1$—C(=S)—, —NHCO—R$_3$—COO—, —OCO—R$_3$—CONH—, —OCO—R$_3$—COO—, —O—P(=O)(OH)—O—, and —O—P(OH)—O—; and Z is a moiety of one of formulas (2) and (3) below:

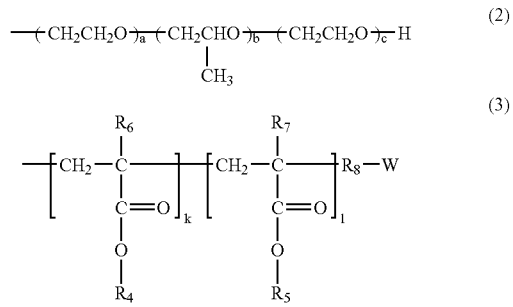

wherein each of $R_1$ and $R_2$ is independently one of a hydrogen atom and a $C_1$–$C_6$ alkyl group; n is an integer from 0 to 6; $R_3$ is selected from the same group for said X; each of a, b, and c is independently an integer from 1 to 20; each of $R_4$ and $R_5$ is independently a $C_1$–$C_{10}$ alkyl group; each of $R_6$ and $R_7$ is independently one of a hydrogen atom and a methyl group; $R_8$ is one of a substituted or unsubstituted $C_1$–$C_{20}$ alkylene group and a substituted or unsubstituted $C_6$–$C_{20}$ arylene group; W is one of —COOH, —NH$_2$, and —OH; and each of k and l is independently an integer from 1 to 10.

2. An ink composition comprising;

a colorant;

an aqueous medium; and at least one of the benzophenone compound of formula (1) below:

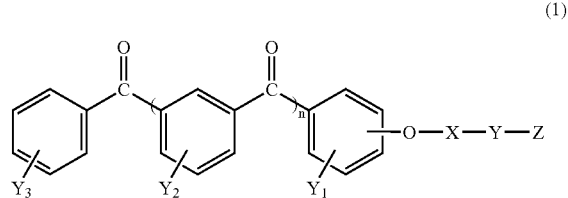

(1)

wherein $Y_1$ is one selected from the group consisting of a H, a OH, an $N(R_1)(R_2)$, a SH, and a substituted or unsubstituted $C_1$–$C_{30}$ heteroalkyl group;

each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

X is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

Y is a linker selected from the group consisting of —O—, —CO—, —$NR_1$—, —N═N—, —S—, —NH—, —CH═CH—, —C≡C—, —C(═O)$NR_1$—, —$NR_1$CO—, —$SO_2$—, —$SO_3$—, —COO—, —OCO—, —C(═S)—O—, —OC(═S)—, —CO—O—CO—, —CO—S—CO—, —CO—$NR_1$—CO—, —C(═S)—O—C(═S)—, —C(═S)—S—C(═S)—, —C(═S)—$NR_1$—C(═S)—, —NHCO—$R_3$—COO—, —OCO—$R_3$—CONH—, —OCO—$R_3$—COO—, —O—P(═O)(OH)—O—, and —O—P(OH)—O—; and Z is a moiety of one of formulas (2) and (3) below:

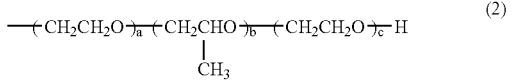
(2)

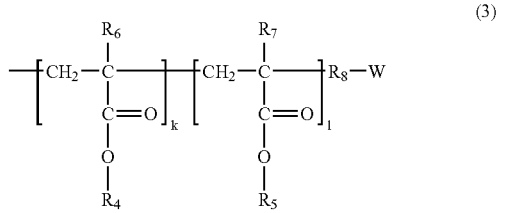
(3)

wherein each of $R_1$ and $R_2$ is independently one of a hydrogen atom and a $C_1$–$C_6$ alkyl group; n is an integer from 0 to 6; $R_3$ is selected from the same group for said X; each of a, b, and c is independently an integer from 1 to 20; each of $R_4$ and $R_5$ is independently a $C_1$–$C_{10}$ alkyl group; each of $R_6$ and $R_7$ is independently one of a hydrogen atom and a methyl group; $R_8$ is one of a substituted or unsubstituted $C_1$–$C_{20}$ alkylene group and a substituted or unsubstituted $C_6$–$C_{20}$ arylene group; W is one of —COOH, —$NH_2$, and —OH; and each of k and l is independently an integer from 1 to 10.

3. The ink composition of claim 2, wherein an amount of the colorant is in a range of 0.1–20 parts by weight with respect to 100 parts by weight of the ink composition.

4. The ink composition of claim 2, wherein an amount of the benzophenone compound is in a range of 0.1–40 parts by weight with respect to 100 parts by weight of the ink composition.

5. The ink composition of claim 2, wherein the aqueous medium is water or a mixture of 5–10% by weight of an organic solvent and 50–95% by weight of water.

6. The ink composition of claim 2, wherein the colorant is at least one selected from the group consisting of carbon black, graphite, vitreous carbon, activated charcoal, activated carbon, anthraquinones, phthalocyanine blue, phthalocyanine green, diazos, monoazos, pyranthrones, perylenes, quinacridones, and indigoid pigments.

7. The ink composition of claim 5, wherein the organic solvent is selected from the group consisting of methyl alcohol, ethyl alcohol, n-propyl alcohol, isopropyl alcohol, n-butyl alcohol, sec-butyl alcohol, t-butyl alcohol, isobutyl alcohol, acetone, methylethyl ketone, diethyl ketone, diacetone alcohol, methyl acetate, ethyl acetate, ethyl lactate, ethylene glycol, diethylene glycol, triethylene glycol, propylene glycol, butylene glycol, 1,4-butane diol, 1,2,4-butane triol, 1,5-pentane diol, 1,2,6-hexane triol, hexylene glycol, glycerol, glycerol ethoxylate, trimethylolpropane ethoxylate, ethylene glycol monomethyl ether, ethylene glycol monoethyl ether, diethylene glycol methyl ether, diethylene glycol ethyl ether, triethylene glycol monomethyl ether, triethylene glycol monoethyl ether, 2-pyrrolidone, N-methyl-2-pyrrolidone, dimethyl sulfoxide, tetramethylene sulfone, and thioglycol.

8. The ink composition of claim 2, further comprising at least one additive selected from the group consisting of a viscosity adjuster, a surfactant, and a wetting agent, wherein an amount of the at least one additive is in a range of 0.5–40 parts by weight with respect to 100 parts by weight of the ink composition.

9. The ink composition of claim 2, wherein at least one benzophenone derivative has the formula (11):

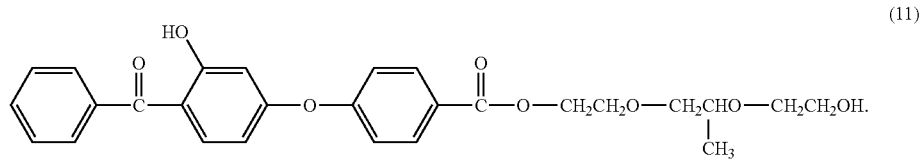
(11)

10. The ink composition of claim 2, wherein at least one benzophenone derivative has the formula (12):

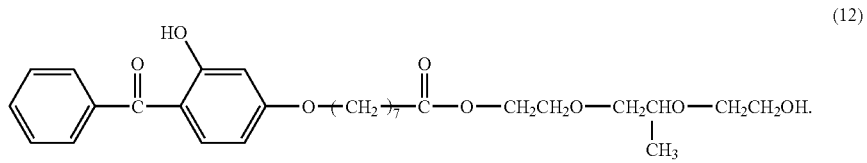

11. The ink composition of claim 2, wherein at least one benzophenone derivative has the formula (14):

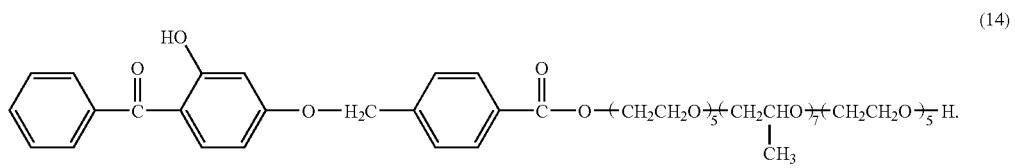

12. The ink composition of claim 2, wherein at least one benzophenone derivative has the formula (15):

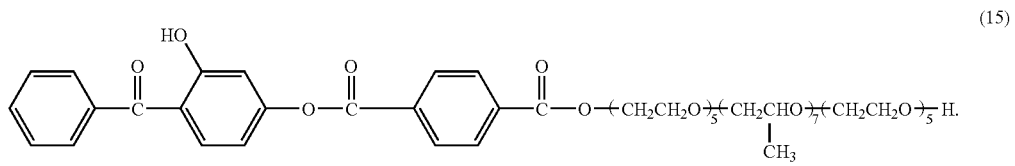

13. The ink composition of claim 2, wherein at least one benzophenone derivative has the formula (17):

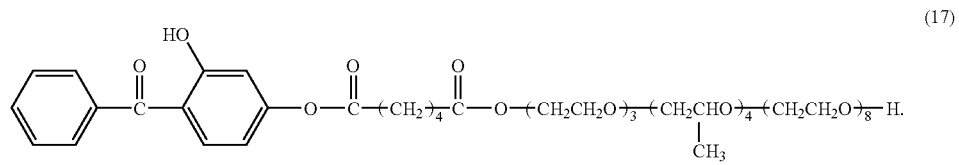

14. The ink composition of claim 2, wherein at least one benzophenone derivative has the formula (18):

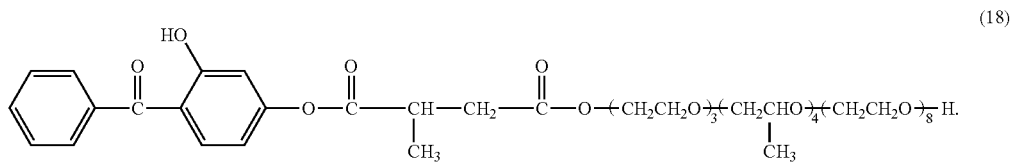

15. The ink composition of claim 2, wherein at least one benzophenone derivative has the formula (19):

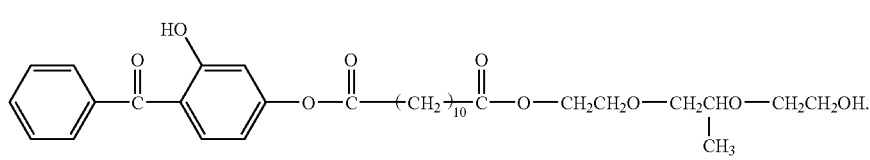
(19)

16. An ink composition comprising:
a colorant;
an aqueous medium; and
at least one benzophenone derivative that has the formula (21):

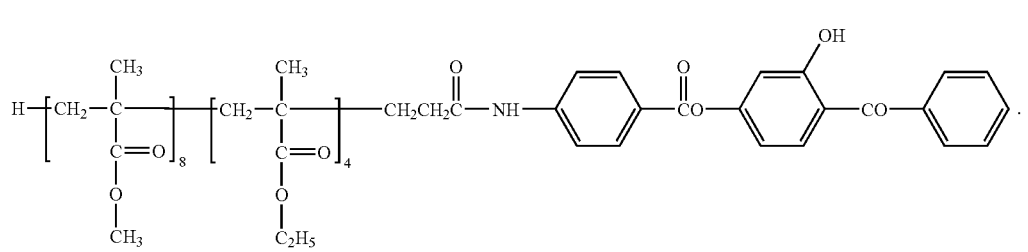
(21)

17. An ink composition comprising:
a colorant;
an aqueous medium; and
at least one benzophenone derivative that has the formula (22):

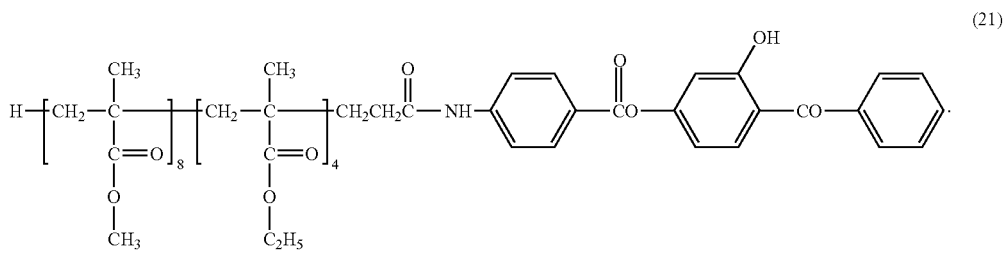
(21)

18. An ink composition comprising:
a colorant;
an aqueous medium; and
a UV light-absorbing benzophenone compound,
wherein the benzophenone compound is represented by formula (1) below:

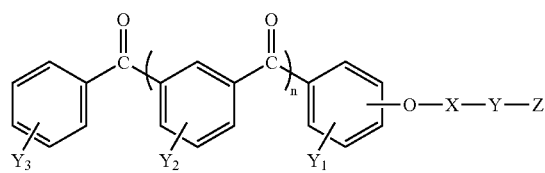
(1)

wherein $Y_1$ is one selected from the group consisting of a H, a OH, an $N(R_1)(R_2)$, a SH, and a substituted or unsubstituted $C_1$–$C_{30}$ heteroalkyl group;

each of $Y_2$ and $Y_3$ is independently selected from the group consisting of a H, a OH, an $N(R_1)(R_2)$, a SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

X is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

Y is a linker selected from the group consisting of —O—, —CO—, —NR$_1$—, —N=N—, —S—, —NH—, —CH=CH—, —C≡C—, —C(=O)NR$_1$—, —NR$_1$CO—, —SO$_2$—, —SO$_3$—, —COO—, —OCO—, —C(=S)—O—, —OC(=S)—, —CO—O—CO—, —CO—S—CO—, —CO—NR$_1$—CO—, —C(=S)—O—C(=S)—, —C(=S)—S—C(=S)—, —C(=S)—NR$_1$—C(=S)—, —NHCO—R$_3$—COO—, —OCO—R$_3$—CONH—, —OCO—R$_3$—COO—, —O—P(=O)(OH)—O—, and —O—P(OH)—O—; and Z is a moiety of one of formulas (2) and (3) below:

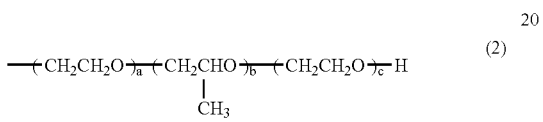
(2)

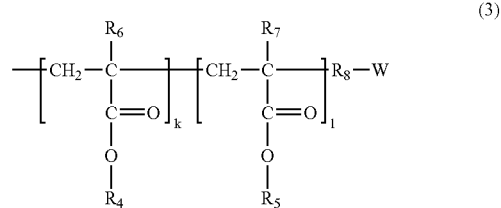
(3)

wherein each of $R_1$ and $R_2$ is independently one of a hydrogen atom and a $C_1$–$C_6$ alkyl group; n is an integer from 0 to 6; $R_3$ is selected from the same group for said X; each of a, b, and c is independently an integer from 1 to 20; each of $R_4$ and $R_5$ is independently a $C_1$–$C_{10}$ alkyl group; each of $R_6$ and $R_7$ is independently one of a hydrogen atom and a methyl group; $R_8$ is one of a substituted or unsubstituted $C_1$–$C_{20}$ alkylene group and a substituted or unsubstituted $C_6$–$C_{20}$ arylene group; W is one of —COOH, —NH$_2$, and —OH; and each of k and l is independently an integer from 1 to 10.

* * * * *

UNITED STATES PATENT AND TRADEMARK OFFICE
CERTIFICATE OF CORRECTION

PATENT NO.        : 7,164,036 B2
APPLICATION NO.   : 10/851124
DATED             : January 16, 2007
INVENTOR(S)       : Kyung-hoon Lee et al.

It is certified that error appears in the above-identified patent and that said Letters Patent is hereby corrected as shown below:

Column 31, Line 29, change "NR1," to --NR1--.

Column 35, Lines 36-49, change

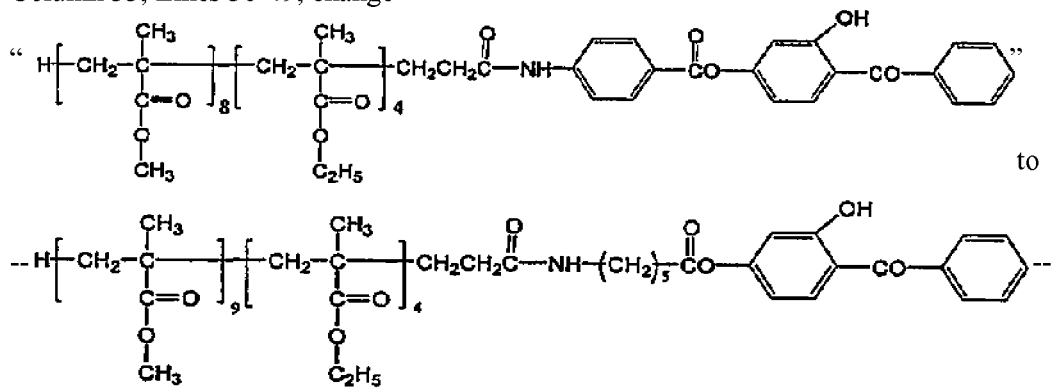

to

Signed and Sealed this

Tenth Day of April, 2007

JON W. DUDAS
*Director of the United States Patent and Trademark Office*